United States Patent [19]

Furukawa

[11] Patent Number: 4,549,549
[45] Date of Patent: Oct. 29, 1985

[54] ELECTRONIC SPHYGMOMANOMETER

[75] Inventor: Toshio Furukawa, Yamatokoriyama, Japan

[73] Assignee: Sharp Kabushiki Kaisha, Osaka, Japan

[21] Appl. No.: 577,483

[22] Filed: Feb. 6, 1984

[30] Foreign Application Priority Data

Feb. 14, 1983 [JP] Japan .................. 58-22608

[51] Int. Cl.⁴ .............................. A61B 5/02
[52] U.S. Cl. .................... 128/680; 128/677
[58] Field of Search ........... 128/672, 677, 680-683

[56] References Cited

U.S. PATENT DOCUMENTS

| 4,188,955 | 2/1980 | Sakamoto et al. | 128/680 |
| 4,273,136 | 6/1981 | Kubo et al. | 128/680 |
| 4,432,373 | 2/1984 | Ogawa et al. | 128/680 |
| 4,461,266 | 7/1984 | Hood, Jr. et al. | 128/680 X |
| 4,475,557 | 10/1984 | Hatschek et al. | 128/680 X |
| 4,501,281 | 2/1985 | Furukawa | 128/677 X |

FOREIGN PATENT DOCUMENTS 49-35798 9/1974 Japan .................. 128/680

Primary Examiner—Lee S. Cohen
Assistant Examiner—Angela D. Sykes
Attorney, Agent, or Firm—Birch, Stewart, Kolasch & Birch

[57] ABSTRACT

An electronic sphygmomanometer includes an auscultatory gap detection system which detects whether the auscultatory gap is detected before the cuff pressure decreases to a preselected value. When the auscultatory gap is detected before the cuff pressure decreases to the preselected value, a time interval for checking for the appearance of the Korotkoff sound is selected longer after the cuff pressure decreases below the preselected value. When the auscultatory gap has not been detected before the cuff pressure decreases to the preselected value, the time interval for checking for the appearance of the Korotkoff sound is selected shorter after the cuff pressure decreases below the preselected value.

14 Claims, 3 Drawing Figures

4,549,549

ELECTRONIC SPHYGMOMANOMETER

BACKGROUND OF THE INVENTION

1. Field of the Invention

The present invention relates to an improvement in an electronic sphygmomanometer.

2. Description of the Prior Art

An example of an electronic sphygmomanometer is disclosed in U.S. Pat. No. 4,273,136, "ELECTRONIC SPHYGMOMANOMETER", issued on June 16, 1981. Generally, in the electronic sphygmomanometer, the arm cuff pressure is first increased to a level higher than an assumed systolic pressure value. A microphone is disposed in the arm cuff to detect the Korotkoff sounds during the decrease of the cuff pressure. When the first Korotkoff sound is detected, the electronic sphygmomanometer memorizes the cuff pressure as the systolic pressure. When the Korotkoff sounds disappear, the system memorizes, as the diastolic pressure, the cuff pressure at a time when the last Korotkoff sound was detected.

That is, the diastolic pressure is determined when the Korotkoff sounds are not detected for a predetermined period of time. However, there is a possibility that the Korotkoff sounds are not detected due to the auscultatory gap even though the cuff pressure is above the diastolic pressure. In such a case an accurate measurement is not achieved.

In order to prevent the erroneous determination caused by the auscultatory gap, a time period, during which the disappearance of the Korotkoff sounds is expected, is selected at a considerably long time in the conventional system. This lengthens the measuring time of the electronic sphygmomanometer. The thus lengthened period will provide noises which are erroneously determined as the Korotkoff sounds. In another conventional system, the Korotkoff sound disappearance determination period is selected longer when the cuff pressure is above a predetermined value, and is selected shorter when the cuff pressure is below the predetermined value. This is based on the assumption that the auscultatory gap scarcely occurs near the diastolic pressure point. However, the assumption is not always correct. More specifically, a person who shows the auscultatory gap near the systolic pressure point shows the auscultatory gap near the diastolic pressure point with a considerably high probability. The above-mentioned first and second conventional systems therefore do not ensure an accurate blood pressure measuring.

OBJECTS AND SUMMARY OF THE INVENTION

Accordingly, an object of the present invention is to provide an electronic sphygmomanometer which ensures an accurate measuring of the blood pressure.

Another object of the present invention is to provide a control circuit in an electronic sphygmomanometer, which controls the blood pressure measuring operation so that an accurate measuring is conducted in the shortest period, and erroneous detection caused by the auscultatory gap is minimized.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

To achieve the above objects, pursuant to an embodiment of the present invention, a determination system is provided for detecting whether the auscultatory gap appears while the cuff pressure decreases to a predetermined level. When the auscultatory gap is detected by the determination system, the Korotkoff sound disappearance determination period is selected longer after the cuff pressure has decreased to the predetermined level. When the auscultatory gap is not observed by the determination system, the Korotkoff sound disappearance determination period is not lengthened even after the cuff pressure has decreased to the predetermined level.

In a predetermined form, the above-mentioned predetermined level is selected at an assumed diastolic pressure value. The assumed diastolic pressure value is calculated through the use of the measured systolic pressure value in accordance with the following formula.

(assumed diastolic pressure value) = $\frac{7}{11}$ × (measured systolic pressure value)

BRIEF DESCRIPTION OF THE DRAWINGS

The present invention will be better understood from the detailed description given hereinbelow and the accompanying drawings which are given by way of illustration only, and thus are not limitative of the present invention and wherein.

DESCRIPTION OF THE PREFERRED EMBODIMENTS

Figure 1:
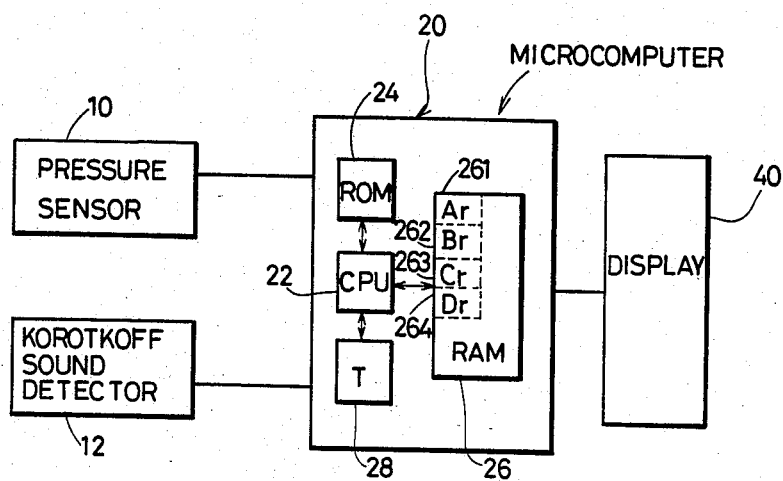
FIG. 1 is a block diagram of an embodiment of an electronic sphygmomanometer of the present invention.

The electronic sphygmomanometer generally includes a pressure sensor 10 and a Korotkoff sound detector 12. The pressure sensor 10 includes a piezoelectric transducer for detecting the cuff pressure. The electronic sphygmomanometer includes, as is well known, a pressurizing member for increasing the cuff pressure over a preselected level before initiating the actual measuring operation. The pressure sensor 10 detects the cuff pressure while the cuff pressure decreases from the above-mentioned preselected level. The Korotkoff sound detector 12 includes a microphone disposed in the arm cuff for developing a pulse signal representative of the Korotkoff sounds.

The cuff pressure data developed from the pressure sensor 10, and the Korotkoff sound pulse signal developed from the Korotkoff sound detector 12 are introduced into a microcomputer 20 of the present invention. The microcomputer 20 determines the systolic pressure and the diastolic pressure in accordance with the pressure data and the Korotkoff sound pulse signal developed from the pressure sensor 10 and the Korotkoff sound detector 12, respectively. The measured systolic pressure and the diastolic pressure are displayed on a liquid crystal display panel 40.

The microcomputer 20 is implemented with an LSI including a central processing unit (CPU) 22, a read only memory (ROM) 24, a random access memory (RAM) 26, and a timer (T) 28. The read only memory (ROM) 24 stores programs for controlling the operation of the electronic sphygmomanometer of the present invention. The random access memory (RAM) 26 includes four registers 261 (Ar), 262 (Br), 263 (Cr), and 264 (Dr). The timer (T) 28 is reset when the Korotkoff sound is detected.

Figure 2:
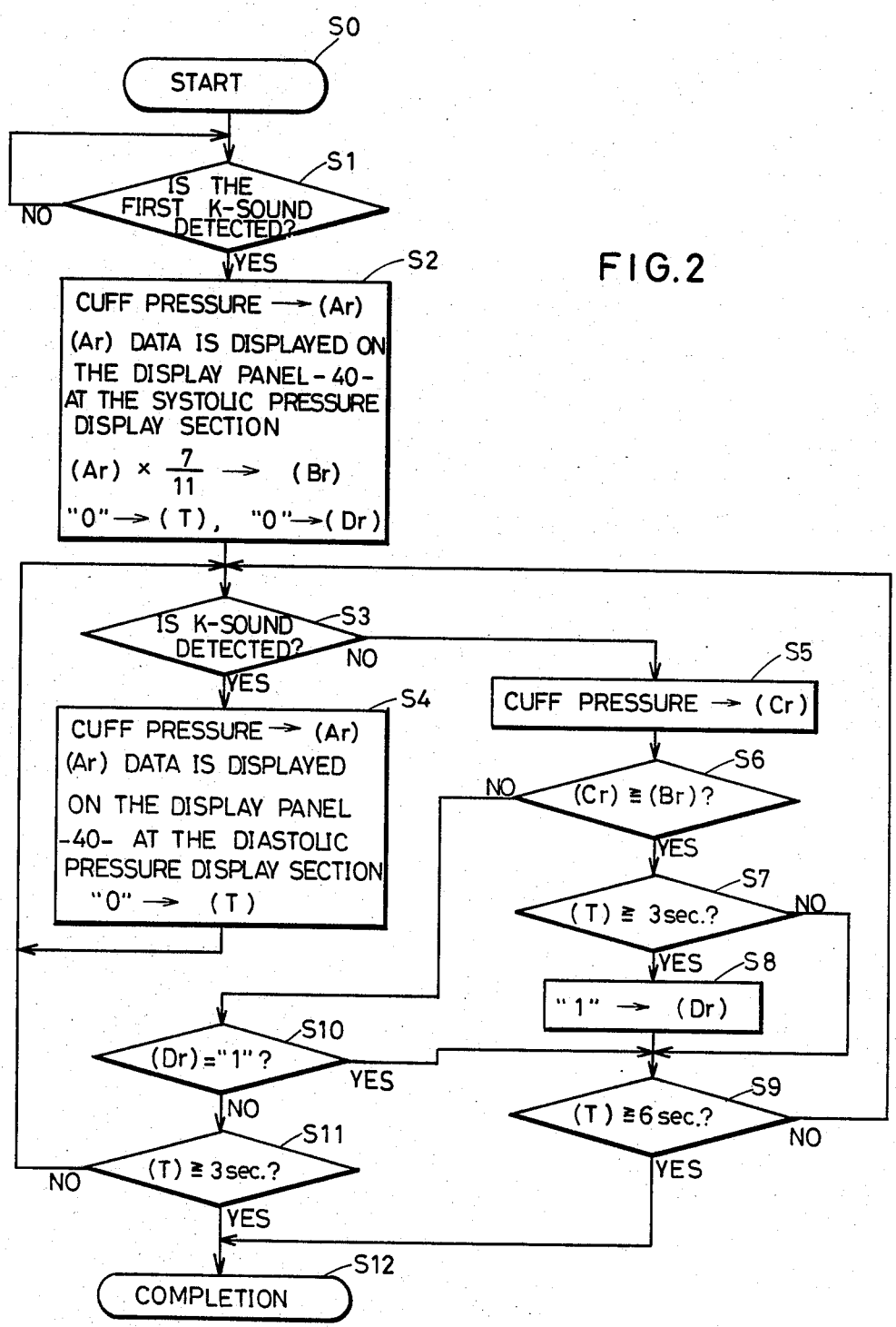
FIG. 2 is a flow chart for explaining an operational mode of the electronic sphygmomanometer of FIG. 1.

An operational mode of the electronic sphygmomanometer of FIG. 1 will be described with reference to FIG. 2. As already discussed above, the cuff pressure is first increased to a level higher than the systolic pressure. The actual measuring operation is conducted after the cuff pressure begins to gradually decrease (step S0). At the following step S1, the first Korotkoff sound is detected. The first Korotkoff sound is detected when the cuff pressure decreases to the systolic pressure point. When the first Korotkoff sound is detected, the operation is advanced to the following step S2. The cuff pressure, at the time when the first Korotkoff sound is detected, is read out and introduced into the first register (Ar) 261. The thus memorized cuff pressure is displayed on the liquid crystal display panel 40 as the systolic pressure. Furthermore, the central processing unit (CPU) 22 conducts a calculation to obtain an assumed diastolic pressure value in accordance with the following formula.

$$(\text{assumed diastolic pressure value}) = \frac{7}{11} \times (\text{systolic pressure value stored in the first register (Ar) -261-})$$

The thus obtained assumed diastolic pressure value is introduced into and stored in the second register (Br) 262. The above formula is determined by rule of thumb. Thereafter, the timer (T) 28, and the fourth register (Dr) 264 are reset.

The following operation is to determine the actual diastolic pressure value. The operation of the steps S3, S5, S6, S7, and S9 is repeated till the next Korotkoff sound is detected. When the Korotkoff sound is detected, the operation is advanced from the step S3 to the step S4, where the cuff pressure at the time when the Korotkoff sound is detected is introduced into and stored in the first register (Ar) 261. The thus memorized cuff pressure is displayed on the liquid crystal display panel 40 as the temporary diastolic pressure value. Then, the timer (T) 28 is reset, and the operation is returned to the step S3. In this way, the temporary diastolic pressure value is gradually reduced to approach the actual diastolic pressure value.

During the flow of the steps S3, S5, S6, S7 and S9, the current cuff pressure is introduced into the third register (Cr) 263 (step S5), and the current cuff pressure stored in the third register (Cr) 263 is compared with the assumed diastolic pressure value memorized in the second register (Br) 262 (step S6). While the current cuff pressure stored in the third register (Cr) 263 is higher than the assumed diastolic pressure value memorized in the second register (Br) 262, the operation is advanced from the step S6 to the step S7.

Under these conditions, when the Korotkoff sound is not detected for three seconds, the operation is advanced from the step S7 to the step S8, where the sign "1" is set in the fourth register (Dr) 264. The sign "1" represents the fact that the auscultatory gap is observed before the cuff pressure is reduced to the assumed diastolic pressure value. The time interval counting conducted by the timer (T) 28 is not interrupted till the next Korotkoff sound is detected. If the Korotkoff sound is not detected for six seconds (step S9), the system determines that the now detected time interval is not the auscultatory gap, and determines that the cuff pressure has already reached the diastolic pressure value. Thus, the measuring operation is completed (step S12) to maintain the last cuff pressure stored in the first register (Ar) 261 as the actual diastolic pressure value. If the Korotkoff sound is detected within six seconds (step S9), the system determines that the now detected time interval is the auscultatory gap. The operation is returned to the step S3 to continue the measuring operation.

When the current cuff pressure introduced into the third register (Cr) 263 becomes lower than the assumed diastolic pressure value stored in the second register (Br) 262 during the measuring operation, the operation flow is changed to a flow including the steps S3, S4, S5, S6 and S10. More specifically, when the sign "1" has already been stored in the fourth register (Dr) 264, the operation is conducted in accordance with the routine including the steps S3, S4, S5, S6, S10 and S9. When the sign "1" is not stored in the fourth register (Dr) 264, the operation is conducted in accordance with the routine having the steps S3, S4, S5, S6, S10 and S11.

That is, when the sign "1" is stored in the fourth register (Dr) 264, the system indicates that the auscultatory gap has been observed before the cuff pressure decreases to the assumed diastolic pressure value. In this case, there is a high possibility that the auscultatory gap appears even after the cuff pressure has reduced below the assumed diastolic pressure value. Therefore, the operation is advanced from the step S10 to the step S9 to check the appearance of the next Korotkoff sound for six seconds. If the Korotkoff sound is detected within six seconds, the operation is advanced from the step S3 to the step S4 to renew the temporary diastolic pressure value stored in the first register (Ar) 261. That is, the system determines that the time interval now detected is the auscultatory gap. When the Korotkoff sound is not detected for six seconds, the operation is advanced from the step S9 to the step S12 to complete the measuring operation. The last data stored in the first register (Ar) 261 is the measured diastolic pressure.

When the sign "1" is not stored in the fourth register (Dr) 264, the system indicates the fact that the auscultatory gap has not been observed till the cuff pressure decreases to the assumed diastolic pressure value. In this case, there is little possibility that the auscultatory gap appears after the cuff pressure has decreased below the assumed diastolic pressure value. Thus, the operation is advanced from the step S10 to the step S11 to check the appearance of the next Korotkoff sound for only three seconds. The temporary diastolic pressure value is renewed upon every detection of the Korotkoff sounds. If the Korotkoff sound is not detected for three seconds, the measuring operation is completed at the step S12.

Figure 3:
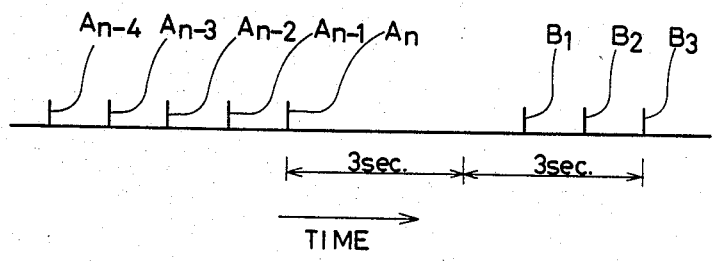
FIG. 3 is a time chart for explaining the auscultatory gap observed by the electronic sphygmomanometer of FIG. 1.

FIG. 3 shows detection pulse An-4, An-3, An-2, An-1 and An derived from the Korotkoff sounds. Now assume that the Korotkoff sound disappears for three seconds after the detection pulse An is developed.

However, the next detection pulse B1 appears before six seconds have passed after the last detection pulse An. In such a case the system determines that the time interval is caused by the auscultatory gap.

In the foregoing embodiment, the sign setting in the fourth register (Dr) 264 is conducted before the cuff pressure has reduced to the assumed diastolic pressure value stored in the second register (Br) 262 (see the step S6). However, the value is not necessarily based upon the above-mentioned assumed diastolic pressure value. It may be a preselected value, for example, 100 mmHg.

In the foregoing embodiment, the actual measuring operation is conducted while the cuff pressure decreases. However, the present invention is applicable to another electronic sphygmomanometer wherein the actual measuring operation is carried out while the cuff pressure gradually increases.

The invention being thus described, it will be obvious that the same may be varied in many ways. Such variations are not to be regarded as a departure from the spirit and scope of the invention, and all such modifications are intended to be included within the scope of the following claims.

What is claimed is:

1. In an electronic sphygmomanometer which measures the systolic pressure and the diastolic pressure while a cuff pressure gradually changes, a measuring control circuit comprising:

storage means for storing a preselected pressure value;

control means for developing a first control signal before the cuff pressure reaches said preselected pressure value during the course of the gradual changing of the cuff pressure, and for developing a second control signal after the cuff pressure reaches said preselected pressure value;

auscultatory gap detection means for detecting the auscultatory gap and for developing a third signal when said auscultatory gap is detected while said first control signal is developed from said control means; and Korotkoff sound detection period determination means for varying a Korotkoff sound detection period in response to said second control signal developed from said control means and said third signal developed by said auscultatory gap detection means.

2. The measuring control circuit of claim 1, wherein said Korotkoff sound detection period determination means lengthens the Korotkoff sound detection period when the third signal has been developed by said auscultatory gap detection means and said second control signal is developed from said control means.

3. The measuring control circuit of claim 2, wherein said Korotkoff sound detection period determination means determines the Korotkoff sound detection period at six seconds when the third signal has been developed by said auscultatory gap detection means and said second control signal is developed from said control means, and at three seconds if the third signal has not been developed by said auscultatory gap detection means and said second control signal is developed from said control means.

4. An electronic sphygmomanometer comprising:
   means for detecting a cuff pressure;
   means for detecting Korotkoff sounds while the cuff pressure gradually decreases from a preset level;
   systolic pressure detection means for storing the cuff pressure when the first Korotkoff sound is detected;
   auscultatory gap detection means for detecting the auscultatory gap and for providing an output signal if the auscultatory gap occurs before the cuff pressure decreases to a preselected value;
   temporary memory means for storing the cuff pressure when the last Korotkoff sound is detected;
   diastolic pressure determination means for determining that said cuff pressure stored in said temporary memory means is the diastolic pressure when the Korotkoff sound is not detected for a preselected period of time; and
   control means for varying said preselected period of time in response to said output signal developed from said auscultatory gap detection means.

5. The electronic sphygmomanometer of claim 4, wherein said control means lengthens said preselected period of time in response to said output signal of said auscultatory gap detection means.

6. The electronic sphygmomanometer of claim 4, wherein said preselected value is a function of the systolic pressure value detected by said systolic pressure detection means.

7. The electronic sphygmomanometer of claim 6, wherein said preselected value is determined in accordance with the fomula:

$$\text{(preselected value)} = \frac{7}{11} \times \text{(systolic pressure value)}$$

8. The electronic sphygmomanometer of claim 4, wherein said auscultatory gap detection means develops said output signal when the Korotkoff sound is not detected for three seconds but is detected within six seconds from the detection of the last Korotkoff sound.

9. In an electronic sphygmomanometer which measures systolic and diastolic blood pressure by detecting Korotkoff sounds:
   first means for determining whether consecutive Korotkoff sounds occur within a selected interval; and
   second means for determining whether the auscultatory gap occurs while measured pressure is above a specified pressure;
   wherein said first means is responsive to said second means for varying said selected interval when said second means determines that the auscultatory gap has occurred above said specified pressure.

10. An electronic sphygmomanometer as in claim 9, wherein said first means is responsive to said second means to lengthen said selected interval.

11. An electronic sphygmomanometer as in claim 10, wherein said first means lengthens said selected interval from 3 seconds to 6 seconds in response to said second means.

12. An electronic sphygmomanometer as in claim 9, wherein said selected interval is an interval of time.

13. An electronic sphygmomanometer as in claim 9, wherein said specified pressure is a function of systolic pressure measured by said sphygmomanometer.

14. An electronic sphygmomanometer as in claim 13, wherein said specified pressure equals 7/11×systolic pressure.

* * * * *